United States Patent [19]

Hijiya et al.

[11] Patent Number: 5,581,009
[45] Date of Patent: Dec. 3, 1996

[54] PROCESS FOR CRYSTALLIZATION OF L-PHENYLALANINE MONOMETHYL SULFATE USING ADDED SALT

[75] Inventors: Toyoto Hijiya; Naoko Sugiyama; Tadashi Takemoto, all of Kawasaki, Japan

[73] Assignee: Ajinomoto Co., Inc., Tokyo, Japan

[21] Appl. No.: 420,499

[22] Filed: Apr. 12, 1995

[30] Foreign Application Priority Data

Apr. 12, 1994 [JP] Japan ................................. 6-073248

[51] Int. Cl.$^6$ ..................... C07C 303/24; C07C 303/42
[52] U.S. Cl. .............................................. 558/43; 562/445
[58] Field of Search ............................... 558/43; 562/445

[56] References Cited

U.S. PATENT DOCUMENTS 4,399,304  8/1983  Matsuishi et al. .
4,803,300  2/1989  Hijiya et al. .
5,118,840  6/1992  Kano et al. .
5,466,864  11/1995  Takemoto et al. .

FOREIGN PATENT DOCUMENTS 0612717  8/1994  European Pat. Off. .

Primary Examiner—Nicky Chan
Attorney, Agent, or Firm—Oblon, Spivak, McClelland, Maier & Neustadt, P.C.

[57] ABSTRACT

A process for improving the yield of crystallization of L-phenylalanine monomethyl sulfate from an aqueous solution containing L-phenylalanine and monomethyl sulfate, by adding an effective crystallization improving amount of a salt of an inorganic or organic acid with an alkali metal, an alkaline earth metal or ammonium, to the aqueous solution.

8 Claims, 2 Drawing Sheets

PROCESS FOR CRYSTALLIZATION OF L-PHENYLALANINE MONOMETHYL SULFATE USING ADDED SALT

BACKGROUND OF THE INVENTION

1. Field of the Invention

The present invention relates to a process for recovering L-phenylalanine (hereinafter abbreviated as L-Phe) as its monomethyl sulfate salt at high yield.

2. Description of the Background

L-phenylalanine and the methyl ester thereof, L-phenylalanine methyl ester (hereinafter abbreviated as L-PM) are important raw materials for peptide synthesis. Particularly, there is a great demand for them as raw materials for a dipeptide sweetener, α-L-aspartyl-L-phenylalanine methyl ester (hereinafter abbreviated to α-APM).

Formerly, various processes for the production of α-APM have been studied. The conventional known industrial processes include a process which comprises reacting N-protected L-aspartic anhydride with L-PM (U.S. Pat. No. 3,786,039) and a process which comprises enzymatic condensation of N-benzyloxycarbonyl-L-aspartic acid and L-PM (Japanese Patent Laying-Open No. 92729/1978).

To obtain L-PM in high purity, a conventional method is used wherein L-Phe is esterified with methanol in the presence of an inorganic acid, such as hydrochloric or sulfuric acid, the resulting acidic reaction solution is neutralized with a suitable base in the presence of water, then the released L-PM is extracted with a water-immiscible organic solvent such as toluene. According to this process, the reaction mixture contains dissolved L-Phe, which remains unreacted in the extract aqueous phase after esterification, and L-Phe, which is produced by decomposition of L-PM upon neutralization and extraction.

L-Phe is a relatively expensive material. Accordingly, it is industrially important to recover any residual L-Phe which fails to be converted, and to reuse it as a raw material. For recovery of L-Phe in the extract aqueous phase of the above-described process, for example, it is recovered as L-phenylalanine monomethyl sulfate salt (hereinafter abbreviated as L-Phe.MeSO$_4$H) (Japanese Patent Laying-Open No. 247913/1994). In recovering L-Phe.MeSO$_4$H, L-tyrosine and D-phenylalanine, which are difficult to efficiently remove as impurities, can be removed with high selectivity by a simple operation and L-Phe.MeSO$_4$H of extremely high optical purity is obtained from a crystallization system of L-Phe of low optical purity and monomethyl sulfate (hereinafter abbreviated to MeSO$_4$H). Thus, this process is excellent as an industrial recovery of L-Phe.

For example, L-Phe.MeSO$_4$H may be separated out by concentration of the extract aqueous phase under acidic conditions when sulfuric acid is used as an acid catalyst. For efficient recovery, however, the aqueous phase should be concentrated to ½ to ⅓ the volume. However, such concentration requires the input of a large amount of energy, decreasing the value of recovering the L-Phe.

When L-Phe.MeSO$_4$H crystals containing impurities are purified by recrystallization from water or slurry-washing, these highly water soluble crystals, can be lost in the mother liquor, resulting in reduced yield.

SUMMARY OF THE INVENTION

Accordingly, one object of the present invention is to provide a process for the crystallization of L-Phe.MeSO$_4$H wherein the solubility of L-Phe.MeSO$_4$H is reduced to improve the yield of crystallization.

A further object of the present invention is to provide an energy efficient method for the recovery of L-Phe.MeSO$_4$H by crystallization.

A further object of the present invention is to provide a method for improving the yield of crystallization of L-Phe.MeSO$_4$H, while maintaining high purity of the recovered product.

These and other objects of the invention have been achieved by the discovery of a process for crystallization of L-Phe.MeSO$_4$H comprising crystallizing L-Phe.MeSO$_4$H in the presence of a salt of an organic or inorganic acid with ammonium or an alkali metal or alkaline earth metal.

DETAILED DESCRIPTION OF THE PREFERRED EMBODIMENTS

Figure 1:
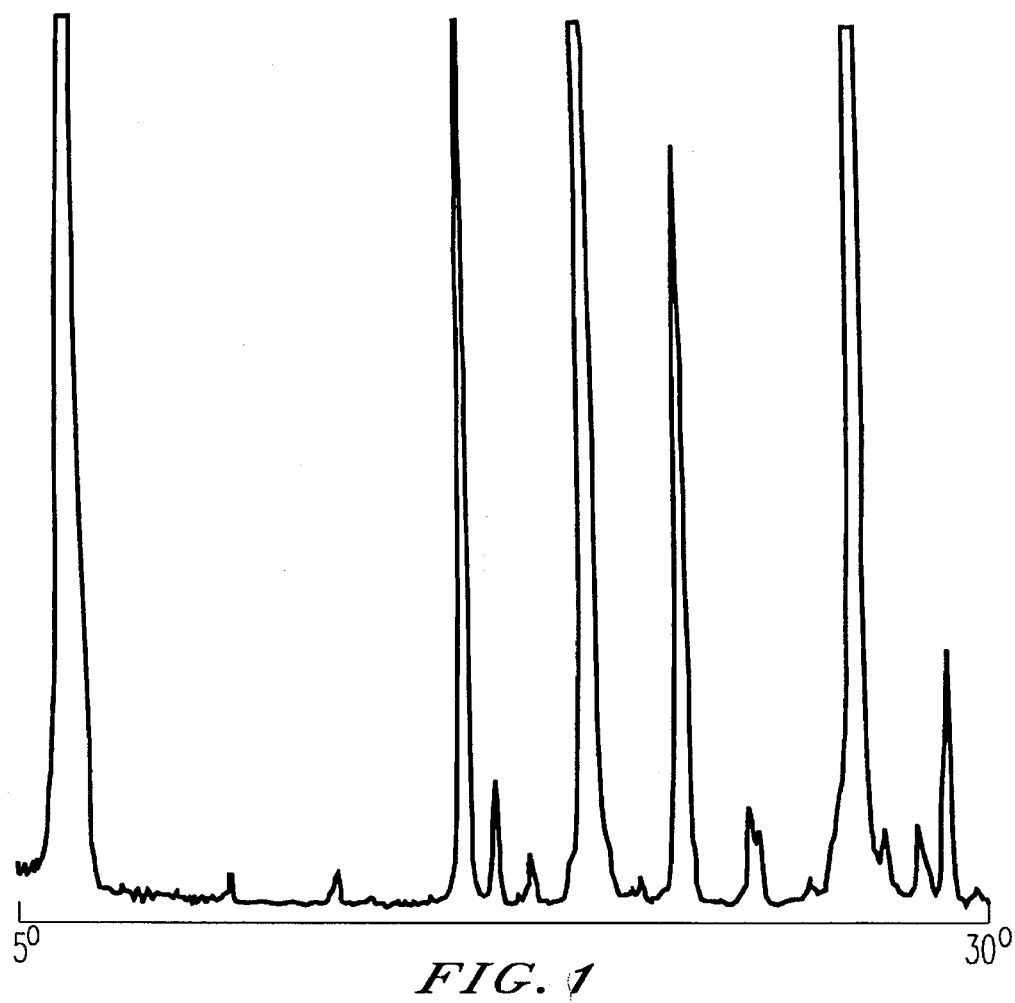
FIG. 1 shows the Powder X-ray diffraction pattern of the L-Phe.MeSO$_4$H crystal obtained in the Production Example (CuKα ray).

The present invention relates to a process for improving the yield of crystallization of L-phenylalanine monomethyl sulfate from an aqueous solution containing L-phenylalanine and monomethyl sulfate, comprising adding an effective crystallization improving amount of a salt of an inorganic or organic acid with an alkali metal, an alkaline earth metal or ammonium, to the aqueous solution. Preferably, the aqueous solution of L-Phe and MeSO$_4$H is prepared by a process comprising esterifying L-phenylalanine and methanol in the presence of sulfuric acid, neutralizing the resultant solution with a base in the presence of water, extracting L-phenylalanine methyl ester with an organic solvent to give an organic layer and an aqueous layer, separating the organic and aqueous layers, and acidifying the aqueous phase to give the aqueous solution.

When L-Phe.MeSO$_4$H is crystallized from the extract aqueous phase, solubility is reduced upon the addition of the salt of the present process. The salt of the present invention provides L-Phe.MeSO$_4$H separated out at high yield without increasing the degree of concentration of the extract aqueous phase.

The salt used in the present process is a salt of an organic or inorganic acid with ammonium or an alkali metal or alkaline earth metal. Suitable salts include alkali metal halides, such as NaCl, and KCl; alkaline earth metal halides such as CaCl$_2$; alkali metal sulfates such as Na$_2$SO$_4$; alkali metal salts of organic (i.e. carbon containing) acids, such as CH$_3$CO$_2$Na, and CH$_3$SO$_4$Na; and ammonium halides such as NH$_4$Cl.

As the concentration of these salts in the crystallization solution increases, ability to reduce the solubility of L-Phe.MeSO$_4$H increases. When NaCl is used (as the cheapest salt for recrystallization or slurry washing of L-Phe.MeSO$_4$H) the effect of the present invention is preferably obtained by using the salt at a concentration of 1 g/dl or more, more preferably 3 g/dl or more. Generally, the preferred lower limit of added salt is 1 g/dl for any of the salts used. When the salt is crystallized from the extract aqueous layer, there already exists a salt produced from the base used for neutralization of the esterified reaction solution and a mineral acid, such as hydrochloric acid or sulfuric acid, which is added for acidification of the extract aqueous layer. In such a case, the present salt is added to further decrease the solubility of L-Phe.MeSO$_4$H. In both cases, however, it is not economical to add salts more than required. Further, when the salt is added in an amount exceeding its own solubility, the separated L-Phe.MeSO$_4$H may be contaminated with the added salt. Accordingly, the upper limit of the amount of the salt to be added is preferably equal to its solubility. Of course, addition of the salt over its solubility will provide a sufficient level of the effect of the present invention, also.

The salts may be used alone or in a combination of two or more.

The salt may be added before or after pH adjustment of the extract aqueous phase, and before or after concentration of the aqueous phase. However, salts which are not neutral should be added before the pH adjustment step, because the pH can be changed by addition of such salts. L-Phe.MeSO$_4$H may be recrystallized in the same way.

The salt may be added as a solid or in the molten state "Molten state", as used herein, means the state wherein the salt is dissolved in water, as well as a reaction solution during the process for production of α-APM containing these salts. Such a reaction solution in the α-ATM process contains, for example:

(i) a mother liquor obtained by hydrolyzing the side flow obtained from production of α-APM under acidic conditions with a mineral acid such as hydrochloric acid, adjusting the pH of the resulting solution to approximately 6 by adding an aqueous alkali solution such as aqueous sodium hydroxide to precipitate L-Phe and removing the L-Phe crystals;

(ii) a mother liquor after L-Asp crystals have been separated out by adjustment of the pH to approximately 3 by addition of an acid, such as hydrochloric acid to the mother liquor of (i); or (iii) a mother liquor after α-APM crystals have been separated, upon neutralization of α-APM hydrochloride crystals with an aqueous alkali, such as sodium carbonate.

Instead of adding salts, an acid component (such as the organic or inorganic acids from which the salts of the present invention are made) and an alkali component (such as the hydroxides of alkali metals, alkaline earth metals and ammonium) can be added separately and neutralized in the crystallization solution to form salts in situ. For example, hydrochloric acid can be added to the crystallization solution, to which is added an equimolar amount of sodium hydroxide, to form sodium chloride.

Having generally described this invention, a further understanding can be obtained by reference to certain specific examples which are provided herein for purposes of illustration only and are not intended to be limiting unless otherwise specified.

EXAMPLES

EXAMPLE 1

To L-Phe.MeSO$_4$H crystals (10 g) suspended in water (20 ml) were added the salts shown in Table 1 (2 g, each). Subsequently, the pH was adjusted to 1.6–1.8, then the solution was stirred at 20° C. overnight. After suction filtration, the concentration of L-Phe in the mother liquor was analyzed by an amino acid analyzer. The results are shown in Table 1.

TABLE 1

| Salts added | Concentration of L—Phe in mother liquor (g/dl) |
|---|---|
| None | 11.8 |
| NaCl | 5.8 |
| KCl | 7.1 |
| CaCl$_2$ | 9.2 |
| NH$_4$Cl | 3.1 |
| Na$_2$SO$_4$ | 9.7 |
| CH$_3$CO$_2$Na | 8.6 |
| CH$_3$SO$_4$Na | 6.5 |

EXAMPLE 2

Esterification was conducted using L-Phe, sulfuric acid and methanol. The reaction solution was neutralized with 15% aqueous Na$_2$CO$_3$, then the resultant L-PM was extracted with toluene to give 1,000 ml of an extract aqueous layer. According to the results of analysis using an amino acid analyzer, the layer contained 7.7 g of L-Phe. After addition of L-Phe (12 g), the pH was adjusted to 1 with sulfuric acid, followed by concentration under reduced pressure to 770 ml. NaCl (15.2 g) was added to 256 ml of the concentrate, and stirred at 5° C. overnight to crystallize then separated by filtration under reduced pressure. The concentration of L-Phe in the separated mother liquor was 0.43 g/dl, and the yield of crystallization as L-Phe was 85.6%.

Comparative Example 1

The procedure of Example 2 was repeated using the concentrate obtained in Example 2 (256 ml), except that NaCl was not added. The concentration of L-Phe in the separated mother liquor was 0.81 g/dl and the yield of crystallization as L-Phe was 70.2%.

EXAMPLE 3

In the same manner as in Example 2, 555 ml of the concentrate was obtained (concentration degree: 1.8 times based on the extract aqueous layer). The concentrate (139 ml) was crystallized at 5° C. overnight and separated. The concentration of L-Phe in the mother liquor was 0.36 g/dl and yield of crystallization as L-Phe was increased to 92.4%.

Water (29 ml) was added to the same concentrate (139 ml) to reduce the concentration (concentration degree: 1.5 times based on the extract aqueous layer). After the same crystallization process, the concentration of L-Phe in the mother liquor was 0.39 g/dl and the yield of crystallization as L-Phe was increased to 89.4%.

Similarly, water (29 ml) was added to the same concentrate (139 ml) to reduce the concentration, to which was further added NaCl (13 g) to crystallize. The concentration of L-Phe in the mother liquor was reduced to 0.26 g/dl, while yield of crystallization as L-Phe was increased to 92.8%, which is almost same as that obtained with the solution concentrated to 1.8 times the concentration of the extract aqueous layer.

EXAMPLE 4

The mother liquor obtained by crystallization of α-APM hydrochloride was heated at 105° C. for 7 hours and hydrolyzed, then adjusted to pH 5.6 with 48% aqueous NaOH and cooled. The crystallized L-Phe was separated.

The mother liquor was adjusted to pH 3.0 with 35% HCl, then L-aspartic acid was separated. The separated mother liquor contained L-Phe and NaCl at the concentration of 1.1 g/dl and 22.2 g/dl, respectively.

The separated mother liquor (220 ml) was added to the extract aqueous layer (1,150 ml, containing 8.88 g of L-Phe) obtained in the same manner as in Example 2, to which was further added L-Phe (12.4 g), then the pH was adjusted to 1.0 with sulfuric acid. After concentration, under reduced pressure to 640 ml, stirring was continued at 5° C. for 3 hours. The separated crystals were removed by filtration to give 61.6 g of crystals and 565 ml of mother liquor. The crystal contained 21.6 g of L-Phe. The concentration of L-Phe in the mother liquor was 0.21 g/dl. Crystallization yield of L-Phe was 94.8%.

Production Example of L-Phe.CH$_3$SO$_4$H

CH$_3$SO$_4$Na (13.4 g, 0.1 mol) and L-Phe (4–13 g, 25 mmol) were added to water (35 ml) and adjusted to pH=0 with sulfuric acid, which was heated and dissolved at about 70° C., then cooled. The separated crystals were removed by suction filtration, washed with a small amount of chilled water, and dried under reduced pressure.

Figure 2:
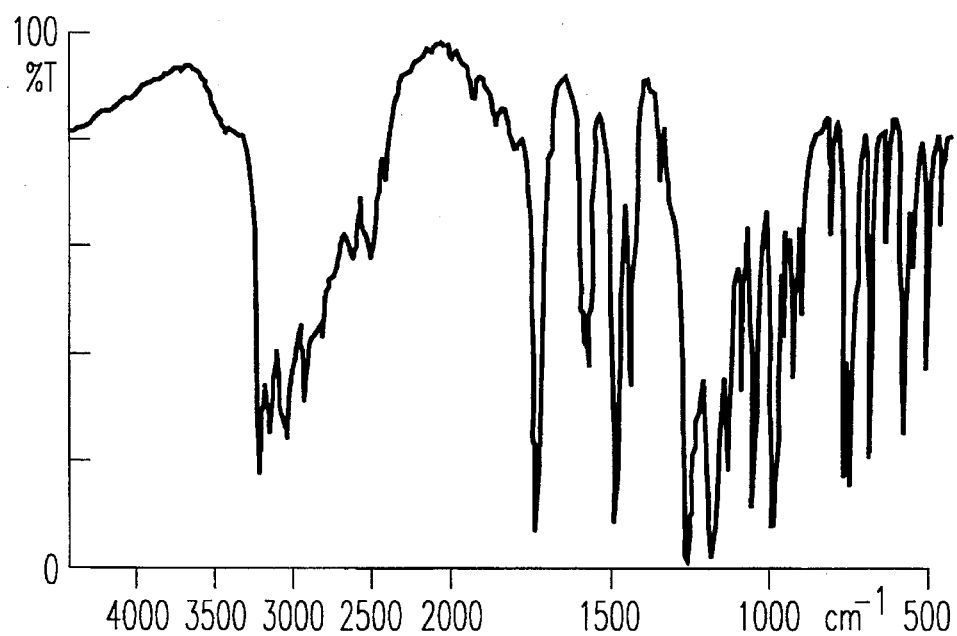
FIG. 2 shows the IR spectrum of the L-Phe.MeSO$_4$H crystal obtained in the Production Example (KBr method).
Figure 3:
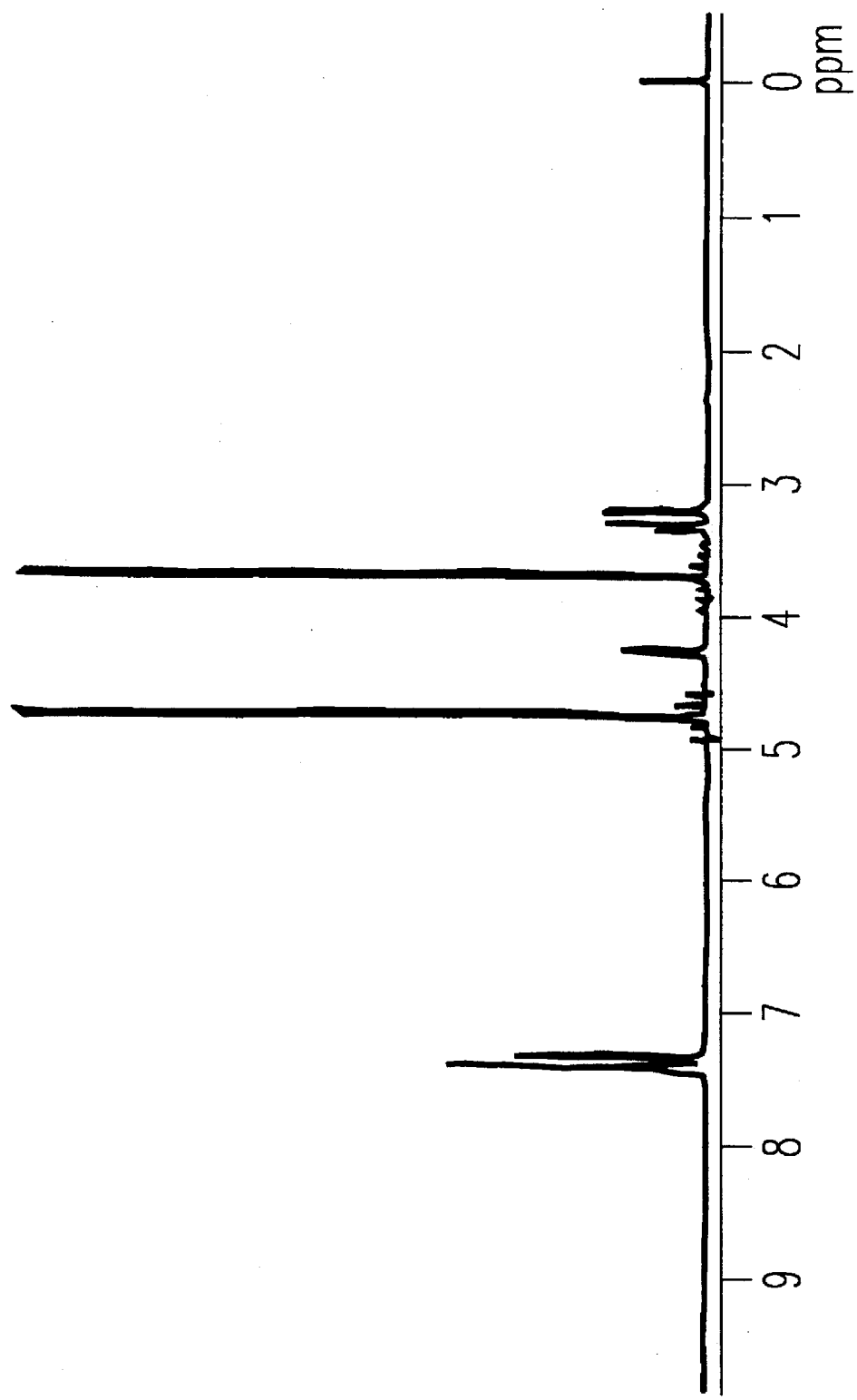
FIG. 3 shows the $^1$H-NMR spectrum of the L-Phe.MeSO$_4$H crystal obtained in the Production Example (solvent: D$_2$O).

Yield, 5.78 g. The crystals were identified as L-Phe·CH$_3$SO$_4$H according to various measurement of physical properties. The results of the measurement are shown in Table 2 and FIGS. 1–3.

|  | Calcd. | Found |
| --- | --- | --- |
| Composition |  |  |
| Carbon Content | 43.3% | 43.0% |
| Nitrogen Content | 5.1% | 5.1% |
| Sulfur Content | 11.6% | 11.2% |
| L—Phe | 59.5% | 60.2% |
| CH$_3$SO$_4$H | 40.4% | 41.3% |
| Water Content | 0.0% | 0.1% |
| Solubility in solvent | Water | Readily soluble |
|  | Methanol | Soluble |
|  | Acetone | Almost insoluble |
|  | Ether | Almost insoluble |
| Property of aqueous solution |  | Acidic |
| Color reaction | Purplish red with ninhydrin | |
| M.P. | 194.4–195.2° C. (decomp.) | |
| Calculated data of the composition was for CH$_3$SO$_4$H.L—Phe | | |

Accordingly, by using the method of the present invention, the crystallization yield of L-phenylalanine monomethyl sulfate can be improved by the simple operation of adding one or more salts during the crystallization process.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for improving the yield of crystallization of L-phenylalanine monomethyl sulfate from an aqueous solution comprising L-phenylalanine and monomethyl sulfate, wherein the aqueous solution comprising L-phenylalanine and monomethyl sulfate is obtained by a process comprising esterifying L-phenylalanine and methanol in the presence of sulfuric acid, neutralizing the resultant solution with a base in the presence of water, extracting L-phenylalanine methyl ester with an organic solvent to give an organic layer and an aqueous layer, separating the organic and aqueous layers, and acidifying the aqueous phase to give the aqueous solution, comprising adding an effective crystallization improving amount of a salt of an inorganic or organic acid with an alkali metal, an alkaline earth metal or ammonium, to the aqueous solution.

2. The process according to claim 1, wherein said salt is a member selected from the group consisting of alkali metal halides, alkaline earth metal halides, alkali metal sulfates, alkali metal salts of organic acids and ammonium halides.

3. The process of claim 1, wherein said effective crystallization improving amount is a concentration ranging from 1 g/dl to the limit of solubility for the salt in the aqueous solution.

4. The process according to claim 1, wherein said salt is added prior to acidifying the aqueous phase.

5. The process according to claim 1, wherein said salt is added after acidifying the aqueous phase.

6. The process according to claim 1, wherein said salt is added as a solid.

7. The process according to claim 1, wherein said salt is added in the molten state.

8. A process for improving the yield of crystallization of L-phenylalanine monomethyl sulfate from an aqueous solution comprising L-phenylalanine and monomethyl sulfate, wherein the aqueous solution comprising L-phenylalanine and monomethyl sulfate is obtained by a process comprising esterifying L-phenylalanine and methanol in the presence of sulfuric acid, neutralizing the resultant solution with a base in the presence of water, extracting L-phenylalanine methyl ester with an organic solvent to give an organic layer and an aqueous layer, separating the organic and aqueous layers, and acidifying the aqueous phase to give the aqueous solution, comprising adding equimolar amounts of (i) an organic or inorganic acid and (ii) an alkali metal hydroxide, an alkaline earth metal hydroxide or ammonium hydroxide, to the aqueous solution, wherein said equimolar amounts are sufficient to prepare, in situ, an effective crystallization improving amount of a salt from the reaction of (i) and (ii).

* * * * *